United States Patent
Diebold et al.

(10) Patent No.: US 9,314,189 B2
(45) Date of Patent: Apr. 19, 2016

(54) EXTRACORPOREAL PHYSIOLOGICAL MEASUREMENT DEVICE

(75) Inventors: Michael Diebold, Berlin (DE); Jens Philipp, Berlin (DE)

(73) Assignee: Biotronik CRM Patent AG, Baar (CH)

(*) Notice: Subject to any disclaimer, the term of this patent is extended or adjusted under 35 U.S.C. 154(b) by 1386 days.

(21) Appl. No.: 12/939,697

(22) Filed: Nov. 4, 2010

(65) Prior Publication Data

US 2011/0112793 A1 May 12, 2011

Related U.S. Application Data (60) Provisional application No. 61/258,623, filed on Nov. 6, 2009.

(51) Int. Cl.
| | |
|---|---|
| *A61B 5/02* | (2006.01) |
| *G01B 11/00* | (2006.01) |
| *A61B 5/11* | (2006.01) |
| *A61B 5/00* | (2006.01) |

(52) U.S. Cl.
CPC . *A61B 5/11* (2013.01); *A61B 5/721* (2013.01); *A61B 5/1128* (2013.01); *A61B 5/681* (2013.01); *A61B 5/6805* (2013.01); *A61B 5/6806* (2013.01); *A61B 2562/0219* (2013.01)

(58) Field of Classification Search
CPC ........... G01P 15/00; G06F 3/01; G06F 3/011; G06F 3/012; G06F 3/014; G06F 3/015; A61B 5/11; A61B 5/1128; A61B 5/681; A61B 2562/0219
USPC .................. 702/141, 150, 190, 191; 356/614; 600/300, 301, 323, 595
See application file for complete search history.

(56) References Cited

U.S. PATENT DOCUMENTS

| | | | |
|---|---|---|---|
| 5,608,895 A * | 3/1997 | Lee ................................. | 703/24 |
| 6,694,167 B1 * | 2/2004 | Ferre et al. .................... | 600/424 |
| 2002/0035317 A1 * | 3/2002 | Cheng et al. .................. | 600/322 |
| 2005/0215912 A1 * | 9/2005 | Freund et al. ................. | 600/485 |
| 2008/0081973 A1 * | 4/2008 | Hoarau ......................... | 600/336 |
| 2008/0183251 A1 * | 7/2008 | Azar et al. ..................... | 607/101 |
| 2009/0012432 A1 * | 1/2009 | Sharf ............................. | 600/588 |
| 2010/0016745 A1 * | 1/2010 | Crump et al. ................. | 600/519 |
| 2010/0210924 A1 * | 8/2010 | Parthasarathy et al. ....... | 600/301 |
| 2011/0006901 A1 * | 1/2011 | Cassidy ..................... | 340/573.1 |

OTHER PUBLICATIONS

Microsoft Memory and Storage, Apr. 25, 2010, http://windows.microsoft.com/en-US/windows7/memory-and-storage.*

* cited by examiner

*Primary Examiner* — Janet Suglo
*Assistant Examiner* — L. Anderson
(74) *Attorney, Agent, or Firm* — ARC IP Law, PC; Joseph J. Mayo (57) ABSTRACT

An extracorporeal physiological measurement device is disclosed, having fastening means for attaching to the body of a person or animal, measurement means for detection of values of a physiological measured variable on the body, and movement-detecting means and measured-value-influencing means connected thereto at the input for influencing the detected measured values before processing or storage as a function of a position or movement status of the body or the measurement device detected by the detection means such that the measured-value-influencing means have a unit for detection of a shift in position between the measurement device and the body.

16 Claims, 7 Drawing Sheets

EXTRACORPOREAL PHYSIOLOGICAL MEASUREMENT DEVICE

RELATED APPLICATION

This patent application claims the benefit of U.S. Provisional Patent Application No. 61/258,623, filed on Nov. 7, 2009, which is hereby incorporated by reference in its entirety.

TECHNICAL FIELD

The present disclosure relates to a physiological measurement device which is to be worn on the body of a person.

BACKGROUND

Physiological measurement devices to be worn on the body are known, e.g., in the form of wrist watches with a pulse-measuring function or blood pressure meters also worn on the wrist or recently also measurement devices worn in a similar way for determining blood oxygen saturation. To some extent, these measurement devices are already in practical use on a wide scale. Measured-value-influencing means are not necessary and are not provided with all such measurement devices. Wrist watches with a pulse-measuring function in particular may also achieve a relatively high precision, which is at any rate completely adequate for the leisure sports area even without such correction means.

In the case of other mobile devices that are worn on the body and have, e.g., optical sensors for determination of oxygen saturation, determination of movement artifacts, and a corresponding correction of the primary measurement result play an important role and constitute a special challenge. It is known that movement sensors (e.g., acceleration meters) may be used to solve this problem. If a significant movement of the device is detected during a certain measurement phase, then the measured values obtained in that phase are discarded.

However, it has been found that these devices still do not operate completely satisfactorily and the wearing habits of the user are also important for their functionality. In particular, errors may occur due to a relatively loose mechanical connection between the body and the measurement device and may lead to deviations in the movement sequences between the two. An attempt to solve these problems by providing fastening means, which are supposed to ensure a tight and constant connection between the body and the measurement device, e.g., through a tight elastic wristband, substantially impair user acceptance (patient compliance) and thus have a negative effect on the market chances of the corresponding devices.

It is also conceivable for movements of a certain body area to be detected directly by a movement sensor (e.g., an acceleration meter) implanted in the body area where the measurement devices are usually worn and to use these movement signals detected either directly or in combination with movement signals detected in a comparable manner on the measurement device to eliminate or discard movement artifacts from primary measurement signals. An implanted movement sensor would be constantly available and could be placed in the body in such a way that it is not detectable from outside the body.

However, many potential users are frightened off from implantation and especially explantation as surgical procedures as well as by the mere idea of having an implant, so that even with this approach, user acceptance, on average, is not satisfactory. Furthermore, the medical cost to implement this approach is relatively high.

However, although analysis of other parameters, e.g., electromyogram (EMG) measurements sensed by surface leads for conduction of muscle activity, can provide information about whether the measurement device is in contact with the proper body area (EMG visible) or not (EMG invisible), such an analysis does not provide information about the amplitude or direction of movement of the measurement device with respect to the body area.

SUMMARY

The present disclosure relates to a physiological measurement device which is to be worn on the body of a human subject (person) or an animal subject, and has corresponding fastening means, such as a fastener, for attaching it to the body and measurement means, such as a detector, for detecting values of a physiological measured variable on the body as well as movement-detecting means, such as a motion detector, and measured-value-influencing means connected thereto at the input end for influencing the detected measured values before they are processed or stored as a function of a position or movement state of the body or the measurement device as detected by the detection means.

A feature of the present disclosure is therefore to provide an improved measurement device of the aforementioned type, which will permit more accurate and more reliable measurements in everyday use in particular and will nevertheless enjoy a high user acceptance.

This feature is achieved by a measurement device having the features of claim 1. Expedient further embodiments of the inventive idea are the subject of the dependent claims.

The disclosure is directed to a measurement device attached as tightly as possible and in a defined manner to the body of the user, preferably having a fastening means that allows a shift in position (relative movement) between the measurement device and the user's body within certain limits with a high user acceptance. It also takes into account the fact that with a corresponding possibility of adjusting the fastening means, different users will select different degrees of connection and thus a shift in position of varying degrees is allowed.

Instead of mechanically affixing the measurement system or detecting movements of the measurement device and the body separately, the movement (shift in position) of the measurement devices on the body is to be detected and the information thereby obtained is to be used to influence, or to control, the physiological measured values thereby detected. Accordingly, the measured-value-influencing means therefore have a device for detecting a shift in position between the measurement device and the body.

The present invention offers the following advantages, particularly in preferred embodiments:

An unpleasant tight mechanical connection of the measurement system to the subject's arm is no longer necessary, so it is possible to respond better to the wishes and habits of the user and patient compliance can thereby be increased. Furthermore, measurement accuracy and also availability of the measured value over time are increased because measurement interruptions caused by movement may fail to occur entirely or may at least be greatly reduced.

In measurement of oxygen saturation by an optical method, for example, movement artifacts have greater dynamics than the actual measured value, so appropriate elimination thereof, which is ensured by the present embodiments, is especially important for the device function.

One embodiment has optical position-detecting means, e.g., a position detector in the manner of an optical mouse in particular for time-dependent determination of the position of a section of the measurement device on a section of a person's body. In particular, this provides for the position-detecting means to have a light or infrared (IR) emitter, a light or IR signal receiving unit for a light or IR pattern reflected by the skin of the person or animal and an evaluation unit connected downstream from the receiving unit for analyzing the light pattern or IR pattern and deriving a position signal therefrom. This embodiment may rely mostly on inexpensive components such as mass produced computer accessories and therefore can be implemented less expensively and more easily.

According to another embodiment, the movement detection means have an acceleration sensor system, and the measured-value-influencing means have an acceleration signal-evaluating unit, and the device for detecting a shift in position is connected to a correction stage downstream from the acceleration-signal-evaluating unit. Physiological measurement instruments with appropriate sensor systems have long been known, so these device components are also available inexpensively as mass-produced products of a well-engineered technology.

In another embodiment, the measured-value-influencing means are for use in deletion or suppression of further processing or transmission of values of the physiological measured variable from a measurement period of time during which a movement of the body or measurement device, or a shift in position between the measurement device and the body in excess of a predetermined amount has been detected. Alternatively, the handling of movement artifacts detected, having been revised with the results of detection of the shift in position between the measurement device and the body, may be such that the measured-value-influencing means perform a calculated correction of values of the physiological measured variable from a measurement period of time during which a movement of the body or the measurement device or a shift in position between the measurement device and the body in excess of a predetermined amount was detected.

In one aspect of these embodiments, the measured-value-influencing means have an influencing program memory for storing control programs or correction programs to be applied to the measured values of the physiological measured variable to be detected, said means for addressing various programs by detection results of the movement detection means, corrected by detection results of the device for detecting a shift in position. In the simplest case, the aforementioned control programs or correction programs may involve conditional deletion commands but also complicated correction methods for calculating movement effects from detected values of the physiological measured variable(s) determined in measurement series in advance. The addressing and application of a corresponding program to the physiological measured variable(s) may be independent of the type (e.g., direction or speed) or absolute value of movements detected. Detection results of the device for detecting a shift in position are taken into account as (additional) correction variables for this purpose.

In another embodiment, which is especially important for practical reasons, the fastening means include a wristband, and the measurement device may be worn as a wristband device. In another embodiment, the measurement device may be integrated into a garment such as a shirt, a vest or a jacket or the like, which at the same time serves as the fastening means. In another embodiment, which may be used for the purposes of sports medicine in particular, the measurement device is integrated into an accessory such as glove or a shoe or the like, which at the same time serves as the fastening means.

EXEMPLARY EMBODIMENT 1

General

The goal is to determine the acceleration of a body extremity, for example.

A measurement unit attached to a wristband is available.

The measurement unit has an acceleration sensor and an optical movement sensor.

Because the measurement unit moves with respect to the body extremity, the signal of the acceleration sensor is subject to error, i.e., it measures movement of the measurement unit and NOT movement of the body extremity.

The optical movement sensor is used for the correction.

The movement sensor detects movement of the measurement unit on the body extremity.

More specifically:

The light source, e.g., a light emitting diode (LED) or laser, illuminates a skin surface.

Light is reflected by the skin surface and captured by an image sensor (e.g., a complimentary metal oxide semiconductor (CMOS) sensor), e.g., as an image line or image area.

The captured image is forwarded to a digital signal processor (DSP) for analysis.

The DSP prepares image data and compares the image with one or more previous images.

From differences in the images, e.g., edges, shifting of patterns, the direction of the movement, and the speed and acceleration of the movement (shown below in FIG. 5A, curve d, signal of the correction unit) of the measurement unit on the body extremity are calculated. The acceleration sensor of the correction unit is calculated with the signal determined by the acceleration sensor. This minimizes (see curve 5A e) measurement error (see curve 5A c) and yields actual acceleration values of the movement of the extremity (see curve 5A a).

In a further embodiment commercially available optical mouse sensors (OMS) are used to measure displacement of the watch over the wrist of the person wearing it to demonstrate feasibility of the concept.

These OMS sensors measure their movement (displacement) over a surface extending in the X and Y directions. The orientation of the displacements can be seen in FIG. 1.

A value for surface quality is available in common OMS enabling to detect the presence or absence of a surface. This value can be used here to detect that the watch is moving in the Z direction, i.e. that it is too far away to perform a measurement. Furthermore, an OMS feature, Automatic Gain Control (AGC), enables them to be used with a wide variety of surfaces from white paper to printed media. X and Y values and a sampling frequency are then used to derive acceleration values, which are then combined with an acceleration measured in the device to give a corrected acceleration value.

The following parameters and their typical values are needed for the acceleration correction.

| Preset Parameters | Preset Value | Dimension | Comment |
|---|---|---|---|
| Acc_Watch_Max_X, Y, Z | ±5 g typical | [m/s$^2$] | For X, Y, Z; range given by acc sensor in device |
| Acc_Watch_Threshold_X, Y, Z | 0.5-20 typical | [m/s$^2$] | Acc_Watch_Measured < Acc_Watch |
| f_sample | 100 typical | [Hz] | Sampling rate for X, Y, Z |
| OMS_v_max_X, Y | 1 | [m/s] | Max. speed "over ground" for OMS to work correctly [2, p. 1] |
| OMS_fps_max | 9000 | — | Max frames per second = max measurements per second [2, p. 1] |
| OMS_cpm_X, Y | 126000 | [n/m] | Counts per meter = resolution [2, p. 1] derived from 3200 cpi [counts per inch] |

| Measured & Derived Parameters | | Dimension | Comment |
|---|---|---|---|
| Acc_Watch_X, Y, Z | Measured | [m/s$^2$] | For X, Y, Z; given by acc sensor in device |
| OMS_Displacement | Measured | [m] | For X, Y, distance moved since last measurement |
| OMS_Speed | Derived | [m/s] | Derived from OMS_Displacement via integration |
| OMS_Acc | Derived | [m/s$^2$] | Derived from OMS_Speed via integration |
| Surface_quality | Measured | — | = 0 if OMS is too far away from surface |
| Acc_Corrected | Derived | [m/s$^2$] | = Acc_Watch + Acc_OMS |

The following program excerpt demonstrates a possible workflow for the correction of the acceleration.
Workflow:
At a frequency of $F_{sample}$ per second, perform measurement of
ACC_Watch and
OMS_Displacement simultaneously
If (Acc_Watch>Acc_Watch_Threshold) and (Surface_Quality=0) then discard, else
Get OMS_Displacement for X,Y
Integrate X, Y values TWICE over time to get from distance via speed to acceleration "over ground" from OMS
Add Acc_Watch and Acc_OMS to get Acc_Corrected
Acc_Corrected is then to be used for further analysis/data storage as desired
To give a numerical example the following is assumed:
A patient having a tremor of typically about 5 Hz
Acceleration of wrist watch Acc_Watch_X,Y,Z≤±2 g
Maximum. movement of the watch ±3 cm around patients wrist (50), induced by the tremor
As an approximation this movement is here regarded to be linear, i.e. in the X-Y plane.
Some points of the movement are assumed faster, so a maximum speed of 0.5 m/s is assumed
A sampling rate $F_{sample}$ of 100 Hz for all channels (Acc_Watch_X,Y,Z; OMS_Displacement X,Y)
For simplicity the sampling rates of acceleration sensors and OMS are assumed to be the same here:
$F_{sample}$=100 Hz yields a measurement every 10 ms
Tremor of 5 Hz yields a rate of 200 ms per cycle
Consequently, there are 20 measurements per cycle
Maximum speed of 0.5 m/s=0.005 m/10 ms=5 mm/10 ms
Thus, maximum OMS_displacement=5 mm per sample
From these values the acceleration can be calculated via an integration operation, allowing the correction of acceleration values measured by the acceleration sensor of the extracorporeal physiological measurement device.

Advantages and expediencies of the present invention are also derived from the following description of exemplary embodiments on the basis of the figures, in which.

DESCRIPTION OF THE DRAWINGS

DETAILED DESCRIPTION

Figure 1:
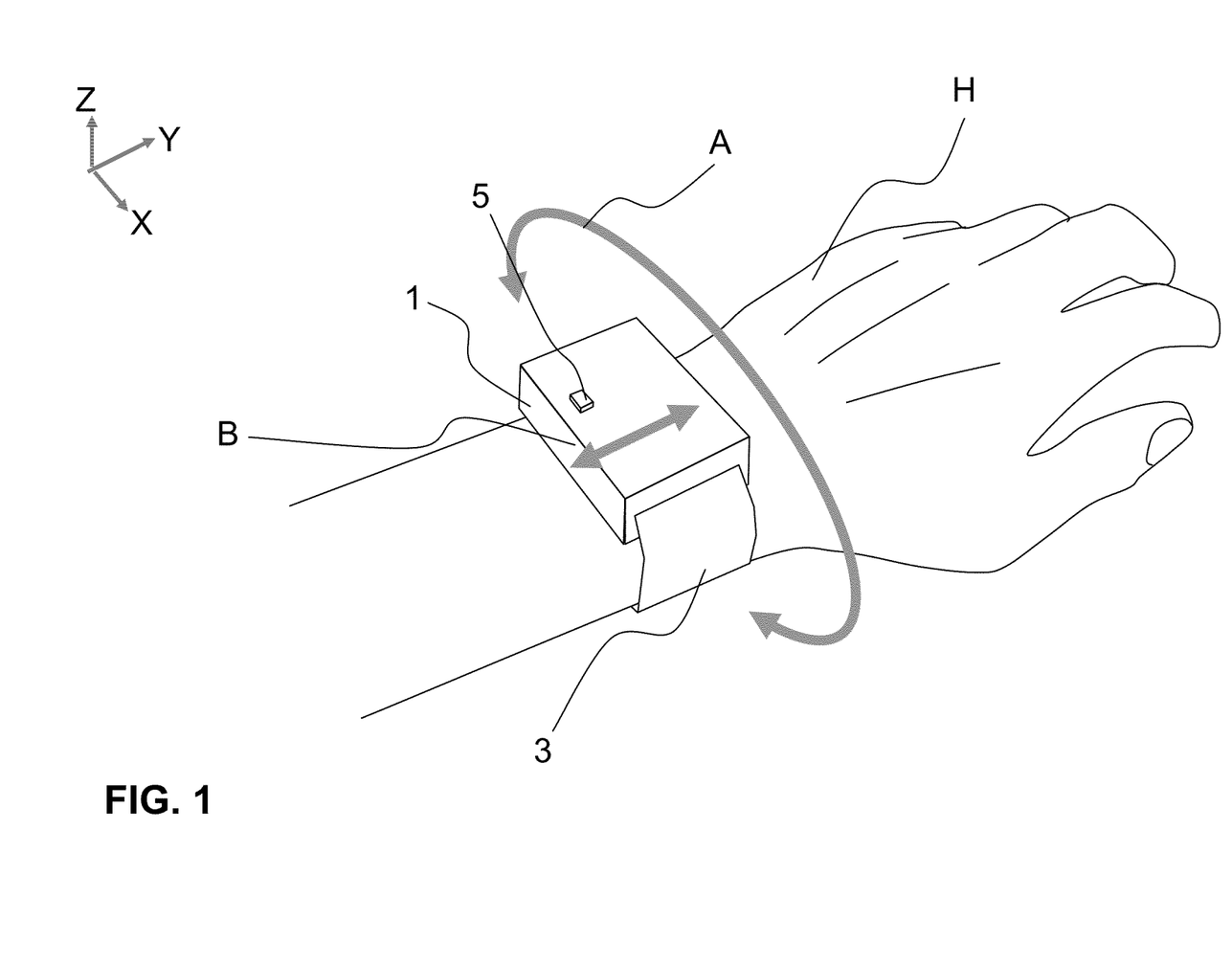
FIG. 1 shows a pictorial perspective view of a physiological measurement device worn on the wrist, with a display of the degrees of freedom of the movement.

FIG. 1 shows a pictorial perspective view of a wristband measurement device 1, which is attached to the wrist of the hand H of a person by means of a wristband 3. Arrows A and B illustrate typical degrees of freedom of movement of such a wristband device with respect to the patient's body, namely a rotational movement (arrow A) and a longitudinal displacement (arrow B) with respect to the arm. An acceleration sensor system 5 of the measurement device 1 detects movement (more precisely, the second lead of the shifts in position in space) of the measurement device, and its output signal may be used for influencing the measured value of physiological measured values of a patient detected by the measurement device 1.

Figure 2:
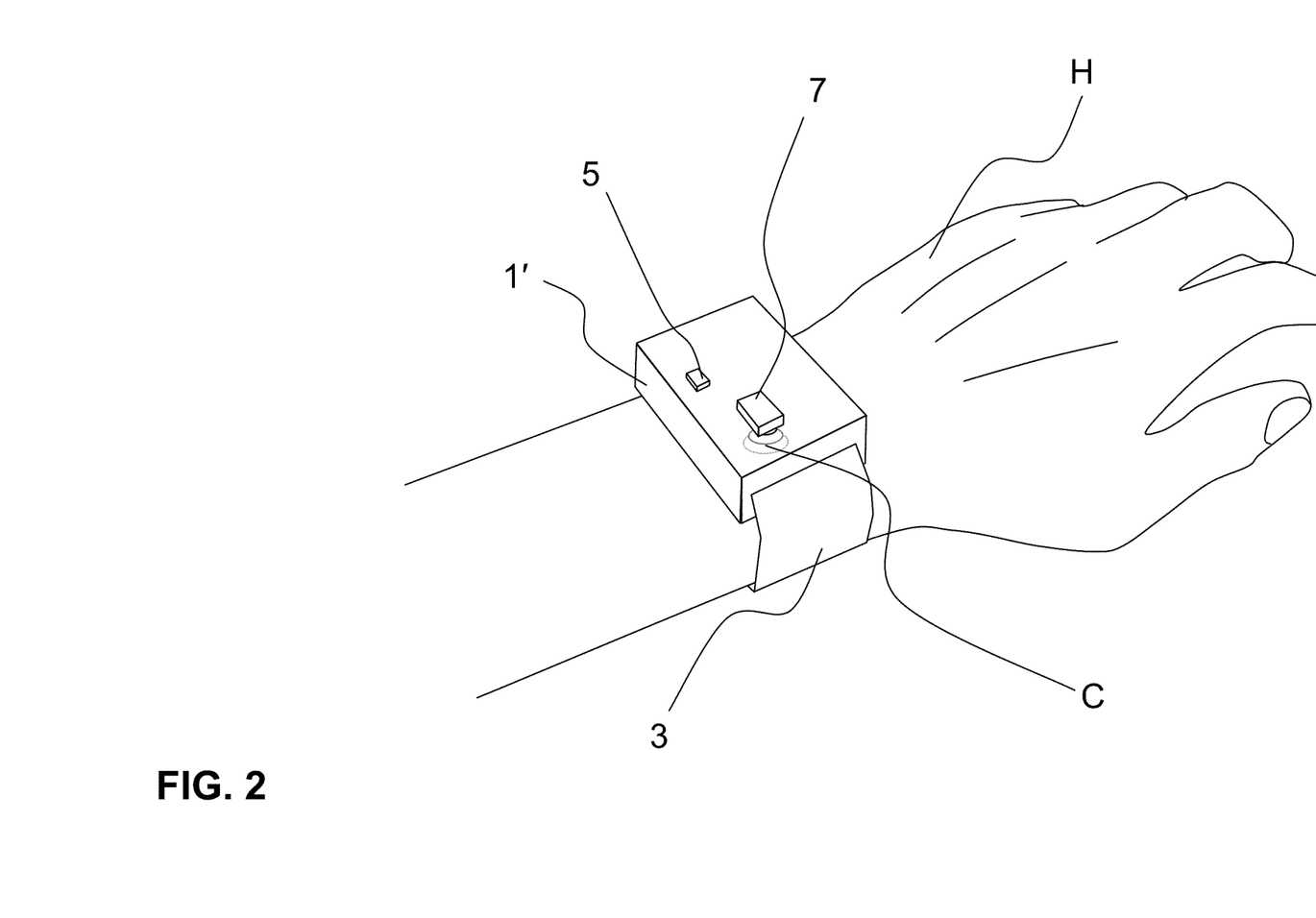
FIG. 2 shows a diagram of an embodiment of the measurement device based on FIG. 1.

FIG. 2 shows a wristband measurement device 1' containing an acceleration sensor system 5 and optical position-detecting means 7 having a detection range or "angle of view" C for additional detection of shifts in position of the measurement device 1' with respect to the body, specifically the user's hand H, as an embodiment that has been modified in comparison with the measurement device 1 according to FIG. 1. The position-detecting means 7 function in the manner of an optical mouse, such as those which have long been known as a computer accessory item.

Figure 3:
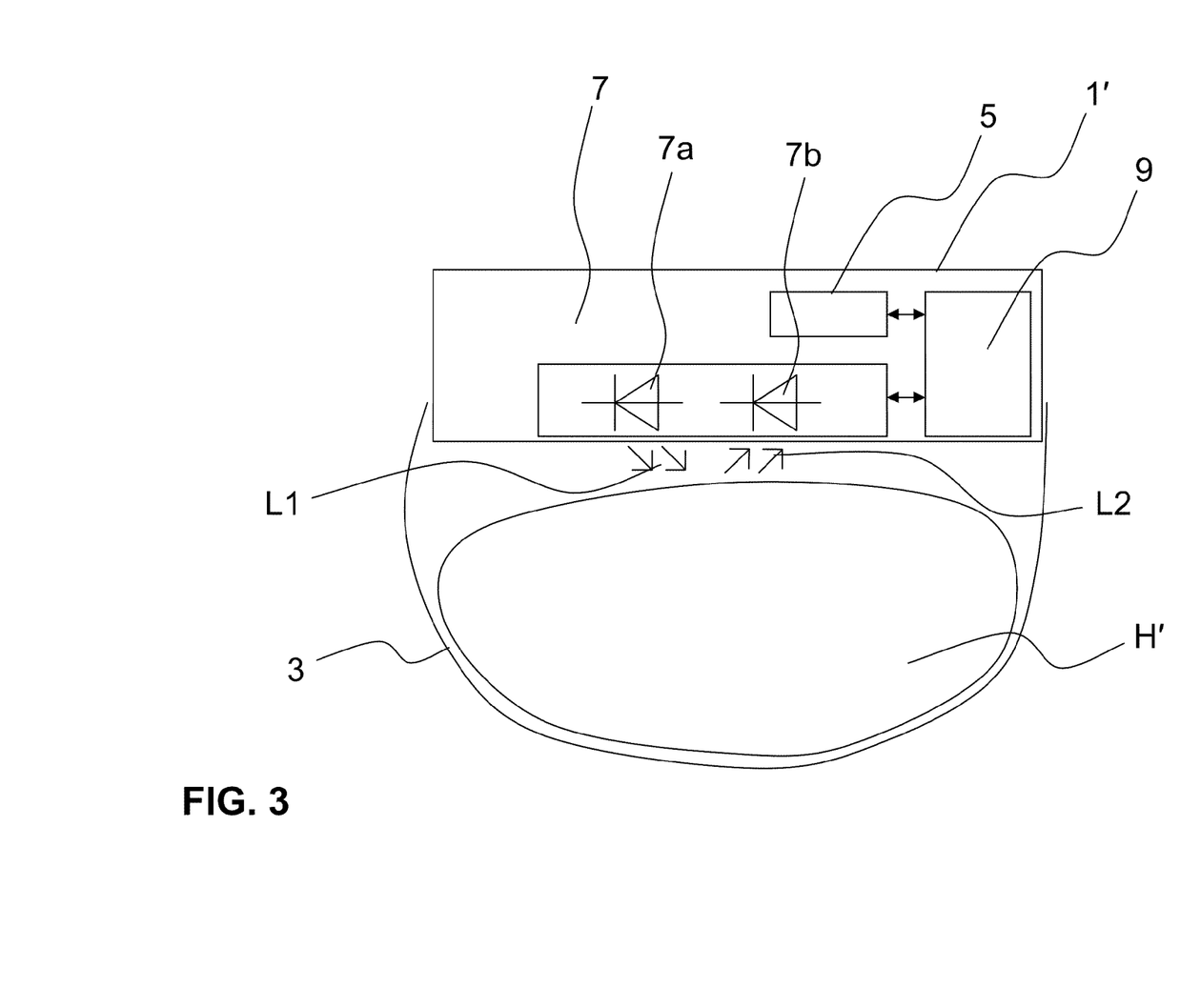
FIG. 3 shows a schematic diagram of essential function components of the measurement device according to FIG. 2.

FIG. 3 shows in somewhat greater detail the wristband measurement device 1' with regard to its essential parts if this figure is to be understood as a schematic diagram corresponding to FIG. 1 and FIG. 3. This figure shows that the optical position-detecting means 7 have a light emitter unit 7a, which emits measurement light L1 in the direction of the user's wrist H', and also a light signal-receiving unit 7b, receiving reflected light L2, reflected by the wrist, and evaluating light L2 with regard to its distribution in space and time to derive a shift-in-position signal, characteristic of a shift in position between the measurement device 1' and the wrist. The light signal-receiving unit 7b comprises a multipart light receiver, e.g., a charge coupled device (CCD) or a CMOS array that is essentially known in its design and function and is not the subject of the present disclosure.

In addition, FIG. 3 shows that the measurement signals of the acceleration sensor system 5 are combined as movement detection means, and the signals of the optical position-detecting means 7 are combined as signals characterizing the shift in position of the measurement device with respect to the user's body in an evaluation unit 9. The evaluation unit 9 supplies a control signal or a calculated correction variable for influencing the physiological measured values using predetermined methods coordinated with the functioning of the actual physiological measurement means of the measurement device 1'.

Figure 4:
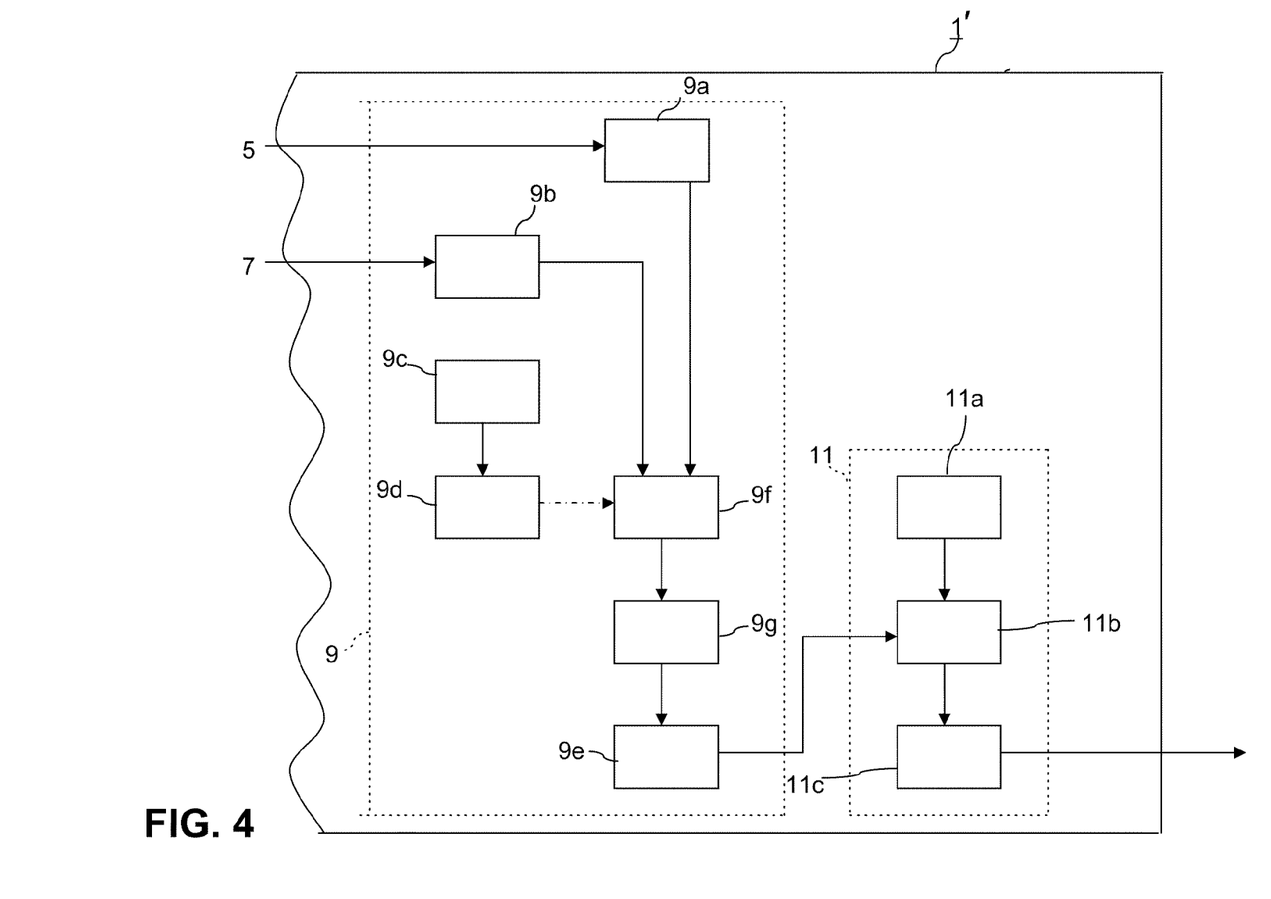
FIG. 4 shows a schematic functional block diagram of another embodiment of the measurement device.

FIG. 4 shows the evaluation unit 9 in greater detail in a partial view of the measurement device 1' in the embodiment described above. In addition to the optical position-determining means 7, evaluation unit 9 forms the measured-value-influencing means of the measurement device 1'. The evaluation unit 9 comprises an acceleration signal-processing unit 9a connected, at its input, to the acceleration sensor system 5 and a position signal-processing unit 9b connected at the input to the optical position-detecting means 7, a time control and synchronization stage 9d connected to a real-time clock 9c and an influencing signal-output stage 9e as interface components on the input or output ends. The principal item of the evaluation unit 9 is an influencing program-selector unit 9f, which is connected at the input to the outputs of the acceleration signal-processing unit 9a and the position signal-processing unit, 9b for use in addressing an influence program memory 9g. At the output end, the influencing signal-output stage 9e is connected to a measurement signal reprocessing stage 11b, which, in the embodiment shown here, is situated between a measurement signal sensor system 11a and the measurement signal transmission stage 11c which together form a physiological measurement component 11 of the measurement device F.

With control by the time-control-and-synchronization stage 9d, the influencing program selector unit 9f combines detected acceleration values and shift-in-position values of the measurement device 1' according to an internally stored evaluation program, which may also include, for example, threshold-value discrimination on the basis of pre-stored threshold values. With the result of this evaluation, it generates an address signal for addressing a memory area of the influencing program memory 9g, in which an influencing program for the physiological measured variable to be monitored by the measurement device 1' is stored, said measurement device 1' or program ensuring a suitable influence (e.g., deletion or suppression of a transmission, or processing, or computer-assisted processing) of the values of the measured variable detected in a relevant period of time during which a significant movement of the measurement device 1' was detected.

Figure 5A:
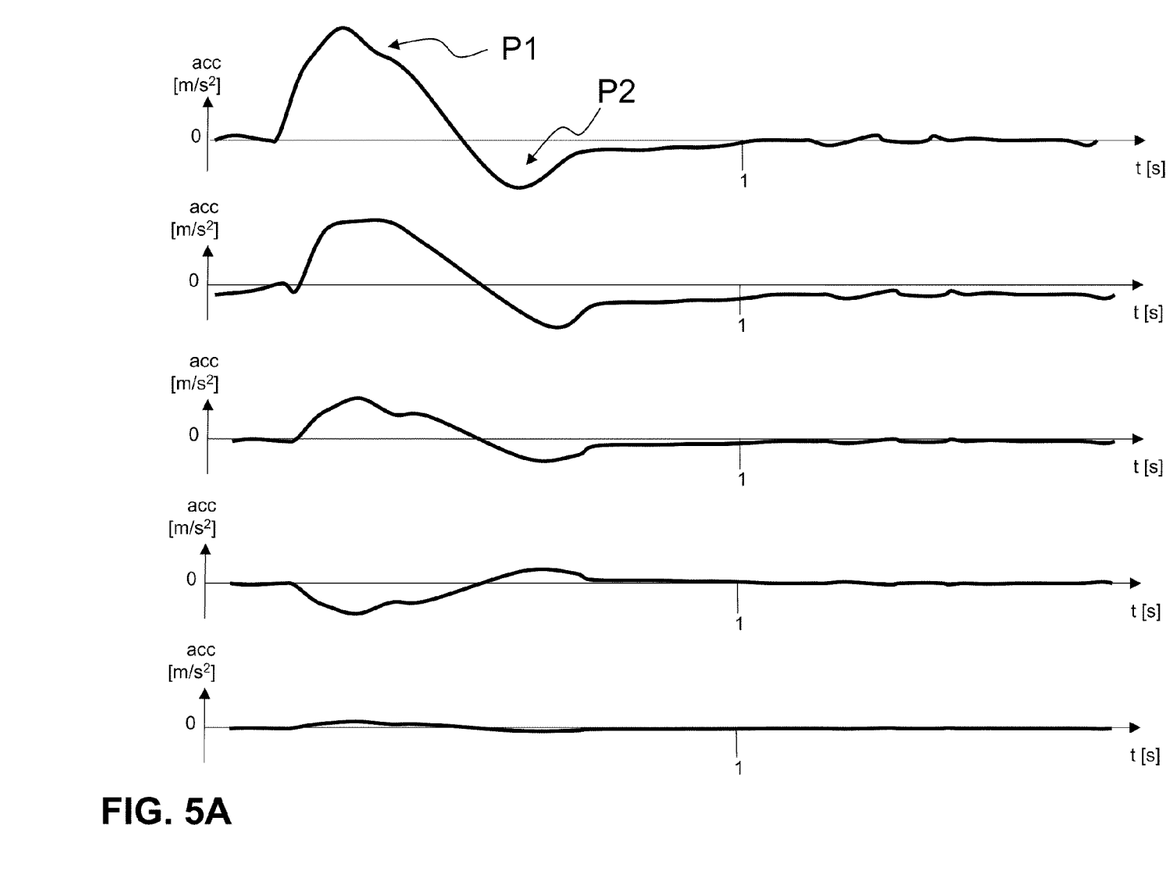
FIGS. 5A and 5B show graphic plots to illustrate the effects of the measurement device.
Figure 5B:
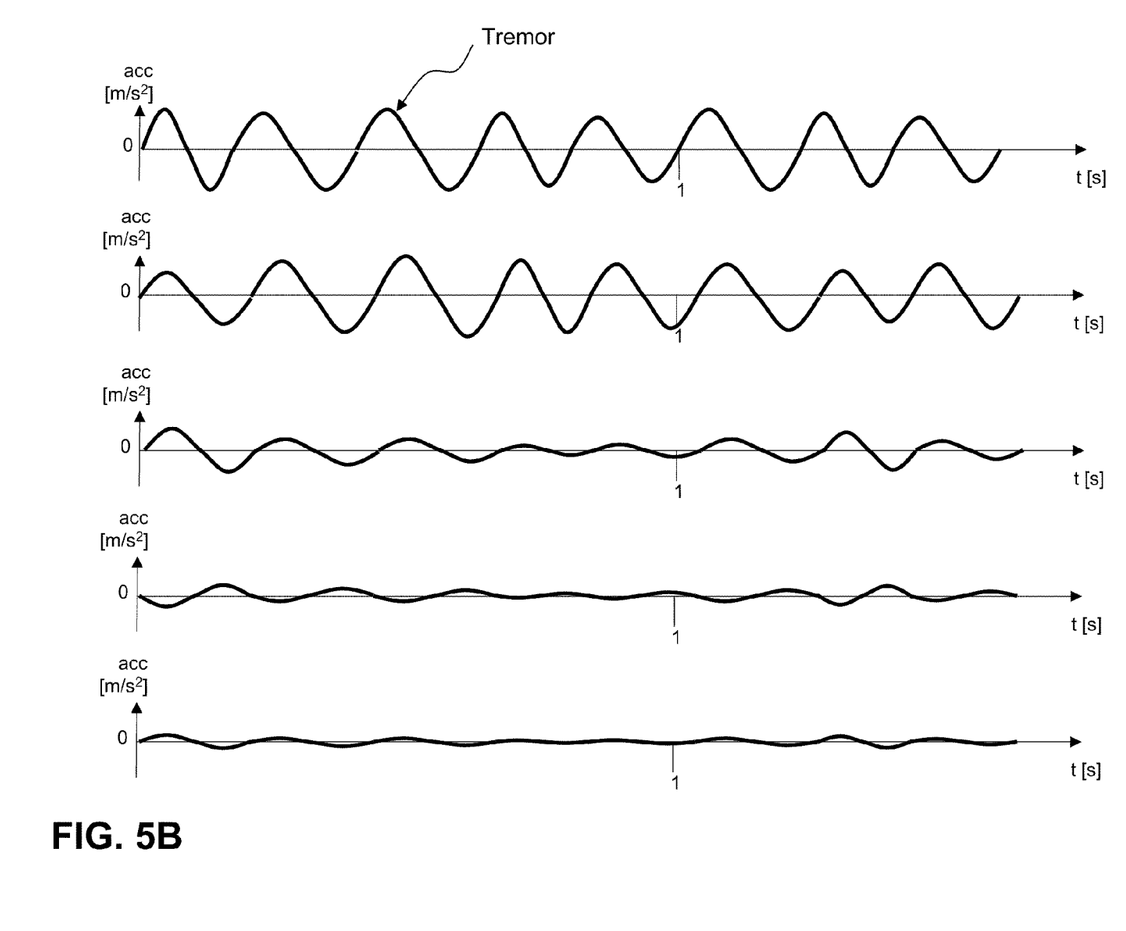

FIGS. 5A and 5B show the operation of one embodiment in graphic plots for two different types of a hand or wrist action, namely for a gripping movement with a rapid start and subsequent deceleration and approach of the hand to a target (FIG. 5A), or a tremor (FIG. 5B). Time is plotted on the abscissa and an acceleration value is plotted on the ordinate. In FIG. 5A, P1 denotes the start of the gripping movement and P2 denotes its deceleration and the approach of the hand to the target.

The top curve shows a chronological characteristic of the acceleration signal in the actual movement of the wrist, the second curve shows the signal measured by the acceleration sensor system 5 on the measurement device 1', the third curve shows an uncorrected measurement error (i.e., difference between the top curve and the second curve), the fourth curve shows a signal of the optical position-detecting means 7, i.e., a signal characterizing the shift in position between the measurement device 1' and the wrist, and finally the last curve shows a corrected measurement error, i.e., the difference between the third curve and the fourth curve. These graphs illustrate that the fully corrected movement-induced measurement error is much smaller than would be expected according to the evaluation of the signal of the acceleration sensor system 5 on the measurement device F. It is self-evident that this is of great importance in the handling of detected measured values of physiological variables potentially subject to a substantial influence due to movement artifacts. This device thus allows a quantitative and possibly also qualitative change in the method of taking into account movement artifacts in such measured values.

Figure 6A:
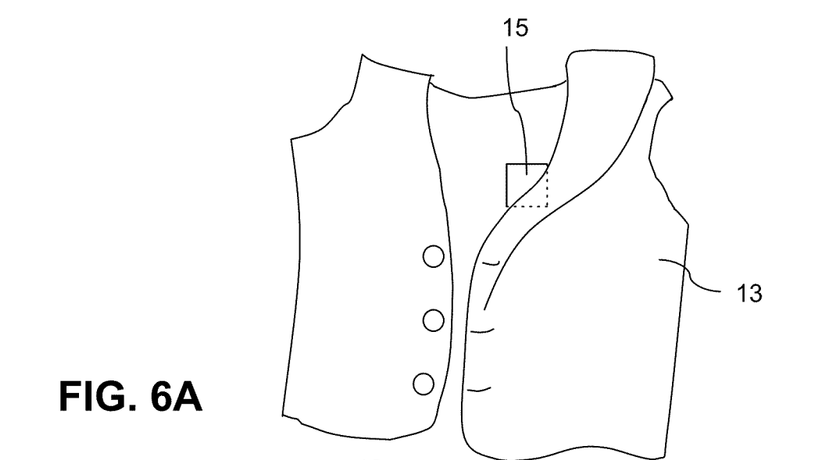
FIGS. 6A and 6B show pictorial views of other embodiments.

As an additional embodiment, FIG. 6A shows a diagram of a measurement device 15 incorporated into a garment such as a vest 13 and optionally containing a suitable acoustic sensor system (not shown) for detection of pulmonary sounds in a patient. Accordingly, it may also be used to suppress or minimize movement artifacts as a result of movements of a patient or test subject wearing the vest. Instead of incorporating the measurement device into a vest, a comparable configuration of the measurement device might also be one in which it is incorporated into a shirt or a jacket or the like, for example.

Figure 6B:
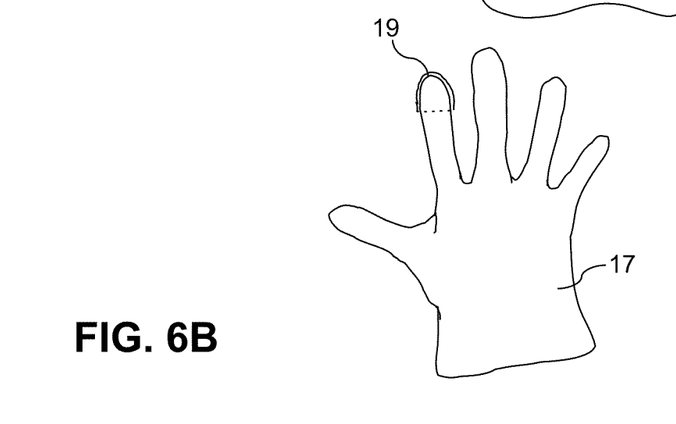

As an additional embodiment, FIG. 6B shows a glove 17 having a measurement device 19, for use in detecting the blood oxygen saturation, incorporated in the area of an index finger. Glove 17 may also have inventive means for elimination or minimization of movement artifacts in a measurement signal of the oxygen saturation sensor system (not shown).

Embodiments of the present invention are not limited to the examples described above and the aspects emphasized above, but instead a variety of modifications which fall within the scope of technical expertise would also be possible.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An extracorporeal physiological measurement device, comprising:
 a fastening device configured to attach the measurement device to a body of a person or animal;
 a measurement device configured to detect values of a physiological measured variable on the body;
 a movement detection device and measured-value-influencing device connected thereto and configured to influence the values detected before being processed or stored as a function of a position or movement status of the body or measurement device as detected by the movement detection device, such that the measured-value-influencing device comprises a device configured to detect a shift in position between the measurement device and the body;
 wherein the measured-value-influencing device is configured to delete or suppress a further processing or a transmission of values of the physiological measured variable from a measurement period of time, in which a movement of the body or measurement device or the shift in position between the measurement device and body in excess of a predetermined measure has been detected;

wherein the measured-value-influencing device further comprises an influencing program memory including control programs or correction programs to be applied to the measured values of the physiological measured variable;

wherein the device configured to detect the shift in position comprises an optical position-detecting device configured to detect a position of a section of the measurement device on a section of the body in a time-dependent manner, the optical position-detecting device comprises an optical mouse; and, wherein the position-detecting device comprises
- a light or IR emitter configured to illuminate a skin surface of the body of the person or animal,
- a light or IR-signal receiving unit configured to capture a light or IR pattern reflected by the illuminated skin of the body of the person or animal,
  - wherein said light or IR pattern is captured as an image line or image area; and
- an evaluation unit downstream from the light or IR-signal receiving unit configured to evaluate the light or IR pattern captured as an image line or image area and derive a position signal therefrom;
  - wherein the evaluation unit comprises an influencing program-selector unit configured to combine detected values from the movement device and the device configured to detect a shift in position according to an internally stored evaluation program in said influencing program memory.

2. The measurement device according to claim 1, wherein the movement detection device comprises an acceleration sensor system and the measured-value-influencing device comprises an acceleration signal-processing unit, and the device configured for detecting a shift in position is connected to a correction stage downstream from the acceleration signal-processing unit.

3. The measurement device according to claim 1, wherein the measured-value-influencing device is further configured to calculate correction values of the physiological measured value from said measurement period of time during which a movement of the body or the measurement device in excess of the predetermined measure or the shift in position between the measurement device and body in excess of the predetermined measure has been detected.

4. The measurement device according to claim 1, wherein said influencing program memory is configured to address various programs by detection results of the movement detection device, corrected by detection results of the device configured to detect the shift in position.

5. The measurement device according to claim 1, wherein said fastening device comprises a wristband, such that the measurement device is configured to be worn as a wristband device.

6. The measurement device according to claim 1, wherein said fastening device is configured to integrate into a garment comprising a shirt, a vest, or a jacket.

7. The measurement device according to claim 1, wherein said fastening device is configured to integrate into an accessory comprising a glove or a shoe.

8. An extracorporeal physiological measurement device, comprising:
- a fastening device configured to attach the measurement device to a body of a person or animal;
- a measurement device configured to detect values of a physiological measured variable on the body;
- a movement detection device and measured-value-influencing device connected thereto and configured to influence the values detected before being processed or stored as a function of a position or movement status of the body or measurement device as detected by the movement detection device, such that the measured-value-influencing device comprises a device configured to detect a shift in position between the measurement device and the body;

wherein the measured-value-influencing device is configured to calculate correction values of the physiological measured value from a measurement period of time during which a movement of the body or the measurement device in excess of a predetermined measure or the shift in position between the measurement device and body in excess of the predetermined measure has been detected;

wherein the measured-value-influencing device further comprises an influencing program memory including control programs or correction programs to be applied to the measured values of the physiological measured variable;

wherein the device configured to detect the shift in position comprises an optical position-detecting device configured to detect a position of a section of the measurement device on a section of the body in a time-dependent manner, wherein the optical position-detecting device comprises an optical mouse; and, wherein the position-detecting device comprises
- a light or IR emitter configured to illuminate a skin surface of the body of the person or animal,
- a light or IR-signal receiving unit configured to capture a light or IR pattern reflected by the illuminated skin of the body of the person or animal,
  - wherein said light or IR pattern is captured as an image line or image area; and
- an evaluation unit downstream from the light or IR-signal receiving unit configured to evaluate the light or IR pattern captured as an image line or image area and derive a position signal therefrom;
  - wherein the evaluation unit comprises an influencing program-selector unit configured to combine detected values from the movement device and device configured to detect a shift in position according to an internally stored evaluation program in said influencing program memory.

9. The measurement device according to claim 8, wherein the movement detection device comprises an acceleration sensor system and the measured-value-influencing device comprises an acceleration signal-processing unit, and the device configured for detecting a shift in position is connected to a correction stage downstream from the acceleration signal-processing unit.

10. The measurement device according to claim 8, wherein the measured-value-influencing device is further configured to delete or suppress a further processing or a transmission of values of the physiological measured variable from said measurement period of time, in which a movement of the body or measurement device or the shift in position between the measurement device and body in excess of the predetermined measure has been detected.

11. The measurement device according to claim 8, wherein said influencing program memory is configured to address various programs by detection results of the movement detection device, corrected by detection results of the device configured to detect the shift in position.

12. The measurement device according to claim 8, wherein said fastening device comprises a wristband, such that the measurement device is worn as a wristband device.

13. The measurement device according to claim 8, wherein said fastening device is configured to integrate into a garment comprising a shirt, a vest, or a jacket.

14. The measurement device according to claim 8, wherein said fastening device is configured to integrate into an accessory comprising a glove or a shoe.

15. The measurement device according to claim 1, wherein the evaluation unit is further configured to compare the capture image line or image area to one or more previous images to determine differences between the image line or image area and the one or more previous images to derive said position signal therefrom.

16. The measurement device according to claim 8, wherein the evaluation unit is further configured to compare the capture image line or image area to one or more previous images to determine differences between the image line or image area and the one or more previous images to derive said position signal therefrom.

\* \* \* \* \*